United States Patent
Yin

(10) Patent No.: US 7,961,838 B2
(45) Date of Patent: *Jun. 14, 2011

(54) COMPUTERIZED TOMOGRAPHY IMAGE RECONSTRUCTION

(75) Inventor: Fang-Fang Yin, Durham, NC (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/287,514

(22) Filed: Oct. 10, 2008

(65) Prior Publication Data

US 2009/0046830 A1 Feb. 19, 2009

Related U.S. Application Data

(63) Continuation of application No. 11/193,160, filed on Jul. 29, 2005, now Pat. No. 7,453,976.

(51) Int. Cl.
*G01N 23/00* (2006.01)

(52) U.S. Cl. .............................. 378/5; 378/9
(58) Field of Classification Search ............... 378/9, 5, 378/4

See application file for complete search history.

(56) References Cited

U.S. PATENT DOCUMENTS

| 6,560,311 | B1 * | 5/2003 | Shepard et al. | 378/65 |
| 6,618,467 | B1 * | 9/2003 | Ruchala et al. | 378/65 |
| 6,819,738 | B2 * | 11/2004 | Hoffman | 378/19 |
| 2003/0048868 | A1 * | 3/2003 | Bailey et al. | 378/65 |
| 2004/0109532 | A1 * | 6/2004 | Ford et al. | 378/57 |

* cited by examiner

*Primary Examiner* — Hoon Song
(74) *Attorney, Agent, or Firm* — Vista IP Law Group, LLP.

(57) ABSTRACT

Systems and methods include coordinated (KV) and mega-electronvolt (MV) computerized tomography (CT) imaging. KV and MV data are combined using a normalization process in order to generate CT images. The resulting CT images can include an improved signal to noise ratio in comparison to CT images generated using either KV or MV imaging alone. The coordinated KV and MV imaging process may be accomplished in significantly less time than using KV or MV imaging alone. This time savings has advantages in treatment verification. The MV projections are optionally generated using MV x-rays configured for x-ray treatment. In these cases the combined projections will reflect the treatment volume.

18 Claims, 9 Drawing Sheets

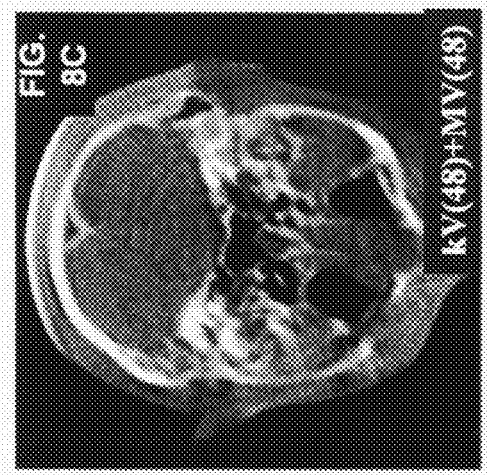
FIG. 8C kV(48)+MV(48)
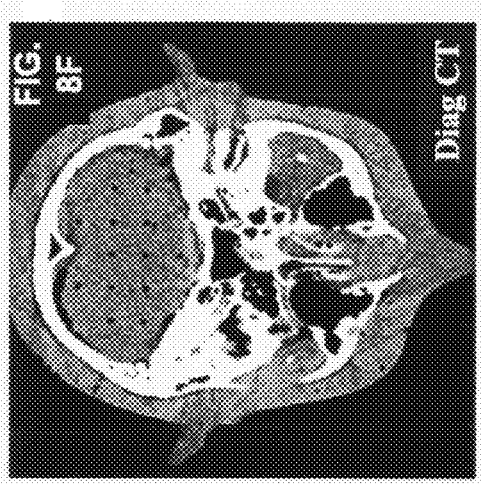
FIG. 8F Diag CT
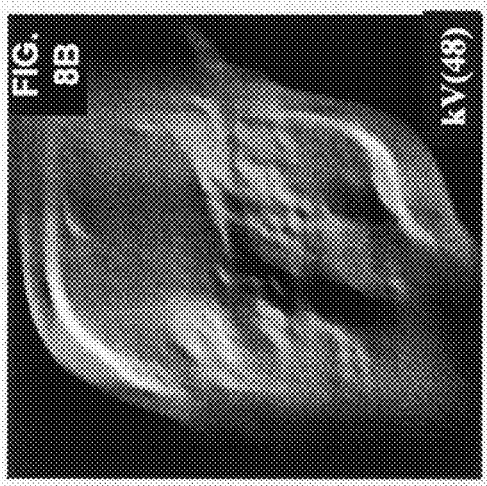
FIG. 8B kV(48)
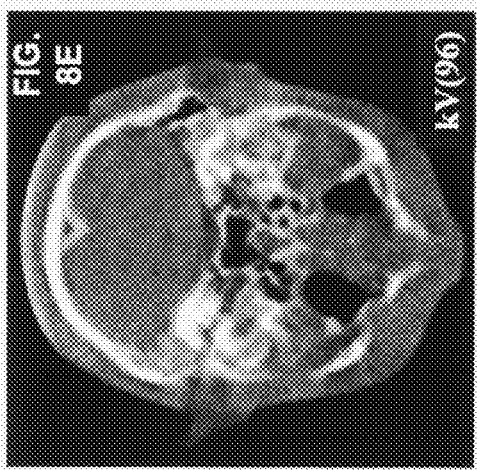
FIG. 8E kV(96)
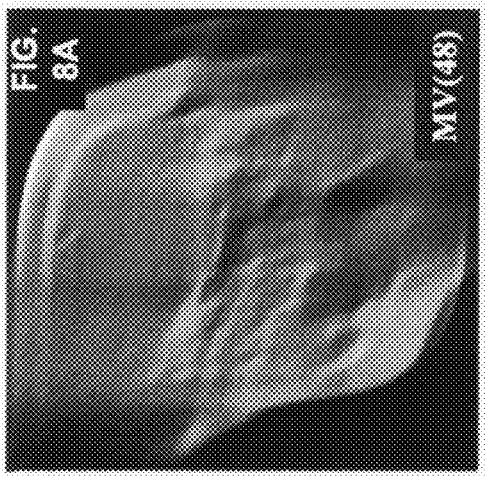
FIG. 8A MV(48)
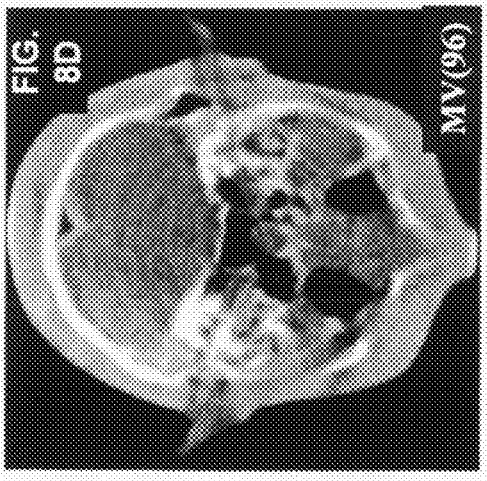
FIG. 8D MV(96)

COMPUTERIZED TOMOGRAPHY IMAGE RECONSTRUCTION

CROSS-REFERENCE TO RELATED APPLICATIONS

This application is a continuation of U.S. Non-Provisional patent application Ser. No. 11/193,160, filed Jul. 29, 2005, now U.S. Pat. No. 7,453,976, the disclosure of which is incorporated herein by reference, which claims priority to and the benefit of U.S. Provisional Patent Application Ser. No. 60/682,170, entitled "A Technique for On-Board CT Reconstruction Using Both Kilovoltage and Megavoltage Beam Projections for 3-D Treatment Verification," filed May 17, 2005, now lapsed, the disclosure of which is incorporated herein by reference.

BACKGROUND

1. Field of the Invention

The invention is in the field of medical imaging and more specifically in the field of computerized tomography.

2. Related Art

Computerized tomography (CT) is an imaging technique wherein x-rays are used to obtain two-dimensional projection images at a variety of different angles around a target being examined. Computer techniques are then used to generate a three-dimensional representation of the target by combining the two-dimensional projection images. The three-dimensional representation can be viewed, sliced and rotated by a user.

CT systems can generally be characterized by the energies of the x-rays used, such as kilovoltage (kV) and megavoltage (MV) imaging. In kV imaging, x-rays with energies in the kiloelectronvolt range are generated and detected. In MV imaging, x-rays with energies in the megaelectronvolt range are generated and detected. Each of these types of imaging has advantages and disadvantages. For example, kV imaging may be subject to interference from tooth fillings and MV imaging may cause radiation damage to the DNA of living cells. MV imaging is sometimes used therapeutically as a cancer treatment.

In diagnostic CT imaging hundreds of two-dimensional projection images are recorded as an x-ray source and detector are rotated around the target. The quality of the final three-dimensional representation is dependent on the number of two-dimensional projection images used to generate the three-dimensional representation. The time required to record hundreds of two-dimensional projection images can be a problem when the target is a patient because the patient must stay still during the imaging process. Typically, diagnostic CT imaging is performed using kV imaging because of the danger to the patient of using MV x-rays to generate so many projection images.

One therapeutic use of MV x-rays is referred to as intensity-modulated radiation therapy (IMRT). IMRT enables caregivers to deliver an extremely conformal dose of high energy x-rays to a well defined treatment volume while minimizing radiation damage to nearby organs and tissues. The success of IMRT is largely dependent on the accuracy of patient positioning and target localization. Therefore, it is important to have an efficient and effective method to confirm the position of the patient and the target volume within the patient. Without confirmation of the position of the target volume, the x-ray dose may harm healthy tissue and miss the tissue requiring treatment. In many situations a volume that is larger than the volume of tissue to be treated is exposed to high energy x-rays in order to compensate for errors in patient positioning, organ motion, and target localization uncertainties. This results in an undesirable exposure of healthy tissue to these x-rays.

There is, therefore, a need for improved methods of imaging that provide greater speed of analysis and greater accuracy for target localization.

SUMMARY

Systems and methods including more than one x-ray source and detector combination are used to generate separate two-dimensional projection images. Each source/detector combination is moved relative to the target in order to create a series of overlapping projection images. By operating each source/detector combination in parallel in time, the time required to generate a series of two-dimensional projection images can be substantially reduced. In comparison to the time requirements and resulting resolution of the prior art, this time savings can be used to generate a three-dimensional representation in a shorter time and/or to generate a three-dimensional representation with better resolution in the same time.

In various embodiments of the invention, the more than one x-ray sources are configured to generate x-rays in different energy ranges. For example, in some embodiments, one source/detector combination is used to generate projection images using kV x-rays while another source/detector combination is used to generate projection images using MV x-rays. These source/detector combinations may operate in parallel. Thus, two different projection images can be obtained at the same time. The projection images generated by one source/detector combination are optionally scaled such that they can be combined with projection images generated by the other source/detector combination. The combined projection images are then used to generate three-dimensional representations of a target.

The three-dimensional representations may be used for target localization. For example, in some instances, therapeutic MV x-rays are used to provide medical treatment while at the same time generating MV projection images of a target area. These MV projection images are combined with kV projection images recorded in parallel with the MV projection images, in order to generate a three-dimensional representation that can be used for real-time target localization.

(copies of independent claims go herexxx)

BRIEF DESCRIPTION OF THE VARIOUS VIEWS OF THE DRAWING

FIGS. 8A-8F are CT images obtained using various imaging modes, according to one embodiment of the invention.

DETAILED DESCRIPTION

Typical embodiments of the invention include two or more x-ray source/detector combinations. Each of these source/detector combinations includes an x-ray source and an x-ray detector. The x-ray source is configured to generate x-rays and direct them toward the associated x-ray detector. The x-ray detector is configured to detect received x-rays in a spatially resolved manner and to generate resulting projection image data. Typically, a target is placed between the x-ray source and x-ray detector for analysis. The detected x-rays are, therefore, representative of a projection of the target onto the x-ray detector. In medical applications, the target is often part of a patient.

Each of the source/detector combinations is configured to image an overlapping volume within the target. For example, in some embodiments, the path of x-rays from a center of an x-ray source to a center of an x-ray detector can be represented by a beam axis, and each source/detector combination is configured such that their respective beam axes intersect in a target region.

Each source/detector combination is optionally operated in parallel to generate projection image data. This parallel operation can be used to reduce the time required to generate a three-dimensional representation of a target and/or increase the resolution of the resulting three-dimensional representation. In some embodiments, parallel operation includes simultaneous generation of x-rays. In some embodiments, parallel operation includes generation of x-rays by one x-ray source while the detector of another source/detector combination is involved in a data transfer process. In these embodiments, the generation of x-rays and data transfer processes may alternate between source/detector combinations. In alternative embodiments, each source/detector combination is operated in series.

In some embodiments, a first source/detector combination is configured to generate x-rays in one energy range while a second source/detector combination is configured to generate x-rays in another energy range. For example, the first source/detector combination can be configured to generate projection image data using kV x-rays while the second source/detector combination can be configured to generate projection image data using MV x-rays. As described further herein, projection image data generated using one energy range is optionally scaled such that it can be combined with projection image data generated using another energy range in order to generate a three-dimensional representation.

In some embodiments, the use of more than one energy range to generate a three-dimensional representation allows for reduction of disadvantages associated with a particular energy range. For example, the use of MV x-rays may reduce the generation of artifacts seen in kV only data, and the use of kV x-rays may reduce injury to tissue surrounding the target volume that would be caused by MV x-rays.

Figure 1:
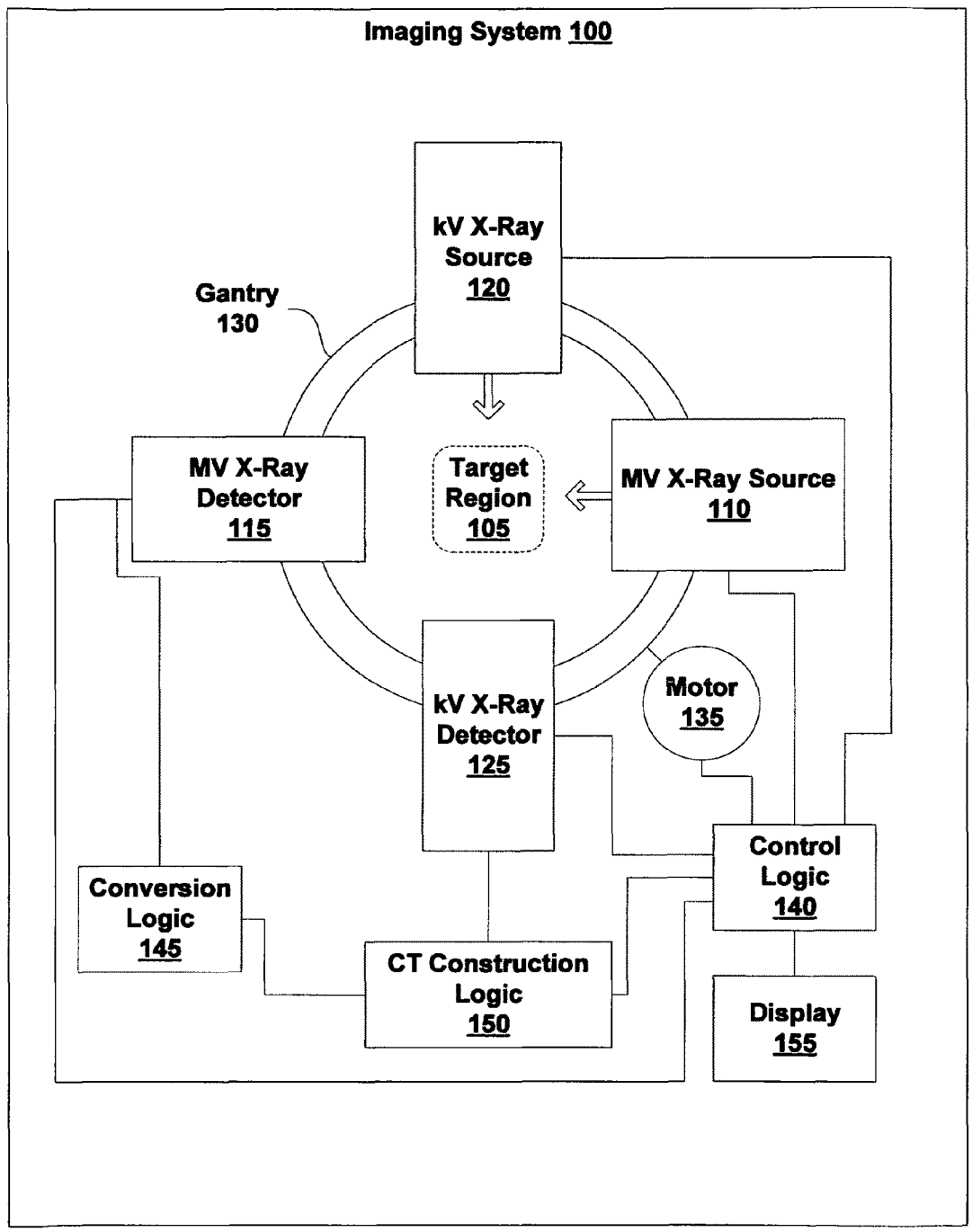
FIG. 1 is a block diagram of an imaging system, according to various embodiments of the invention.

FIG. 1 is a block diagram of an Imaging System 100 configured to generate a three-dimensional representation of a target positioned in a Target Region 105, and optionally configured to provide a therapeutic dose of x-rays to a treatment region within Target Region 105. The instance of Imaging System 100 illustrated in FIG. 1 includes two source/detector combinations. A first combination, referred to as the MV detector/source combination, is configured to generate projection image data using MV x-rays. The MV detector/source combination includes a MV X-Ray Source 110 and a MV X-Ray Detector 115 disposed such that their associated beam axis passes through Target Region 105. A second combination, referred to as the kV detector/source combination, is configured to generate projection image data using kV x-rays. The kV detector/source combination includes a kV X-Ray Source 120 and a kV X-Ray Detector 125 disposed such that their associated beam axis intersects the beam axis of the MV detector/source combination within Target Region 105.

In typical embodiments, MV X-Ray Source 110, MV X-Ray Detector 115, kV X-Ray Source 120 and kV X-Ray Detector 125 are coupled to a movable Gantry 130. Gantry 130 is configured to rotate around Target Region 105 under the control of Motor 135. In alternative embodiments, Motor 135 is configured to rotate a target within Target Region 105. In these embodiments, Gantry 130 is optionally stationary. The kV detector/source combination is optionally rotated around Target Region 105 independent of the MV detector/source combination.

Imaging System 100 further includes a Control Logic 140 configured for operating Motor 135, MV X-Ray Source 110, MV X-Ray Detector 115, kV X-Ray Source 120, and kV X-Ray Detector 125. Control Logic 140 typically includes a processor and memory configured for storing projection image data. Control Logic 140 is further configured to control an optional Conversion Logic 145, a CT Construction Logic 150 and an optional Display 155.

Conversion Logic 145 is configured to scale projection image data received from MV X-Ray Detector 115 such that the scaled data can be combined with projection image data received from kV X-Ray Detector 125. In alternative embodiments, Conversion Logic 145 is configured to scale projection image data received from kV X-Ray Detector 125 such that the scaled projection image data can be combined with projection image data received from MV X-Ray Detector 115. The scaling can include logarithmic functions known in the art. The operation of Conversion Logic 145 is described further elsewhere herein.

CT Construction Logic 150 is configured to construct a three-dimensional representation of a target using two-dimensional projection images of the target generated using both MV X-Ray Detector 115 and kV X-Ray Detector 125. The construction process can be performed using several alternative construction techniques known in the art. For example, in various embodiments, the filtered back-projection technique or multi-level scheme algebraic reconstruction technique (MLS-ART) are used for construction of a three-dimensional representation.

Optional Display 155 is configured for viewing various data generated using MV X-Ray Detector 115 and kV X-Ray detector 125, and for viewing three-dimensional representations of a target constructed using CT Construction Logic 150. Typically, three-dimensional representations are viewed as cross-sections of the three-dimensional representation. These cross-sections are referred to as CT images.

Figure 2:
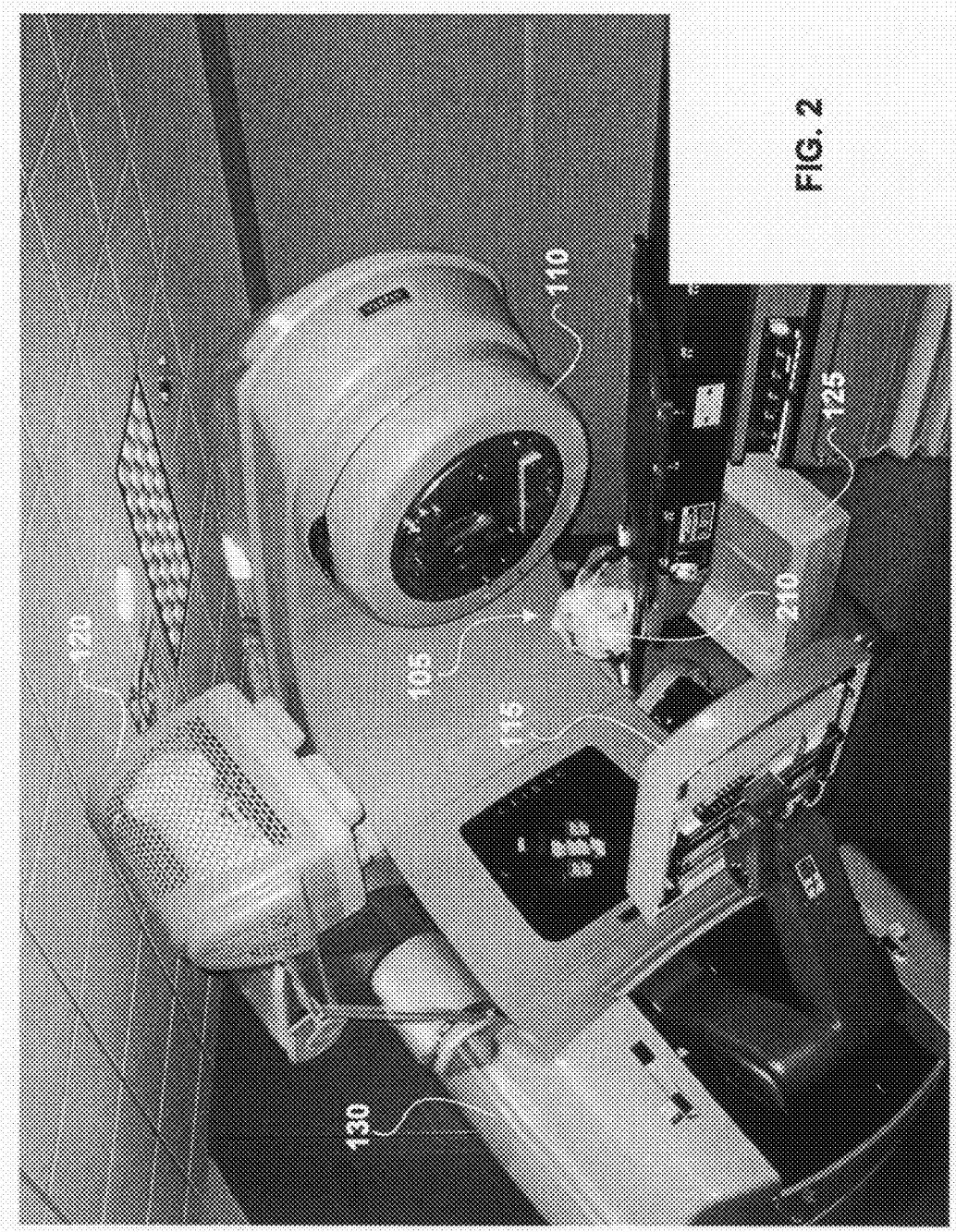
FIG. 2 is a photograph showing of parts of the imaging system of FIG. 1, according to one embodiment of the invention.

FIG. 2 is a photograph showing of parts of Imaging System 110, according to one embodiment of the invention. The MV source/detector combination and kV source/detector combination are positioned such that their respective beam lines intersect at approximately a right angle in Target Region 105. FIG. 2 shows an experimental instance of a Target 210 positioned within Target Region 105. As is discussed further herein, this experimental instance of Target 210 includes a simulation of part of a human head and a device used to study resolution in x-ray imaging. In practice, the instance of Target 210 shown in FIG. 2 is typically replaced by a patient.

Figure 3:
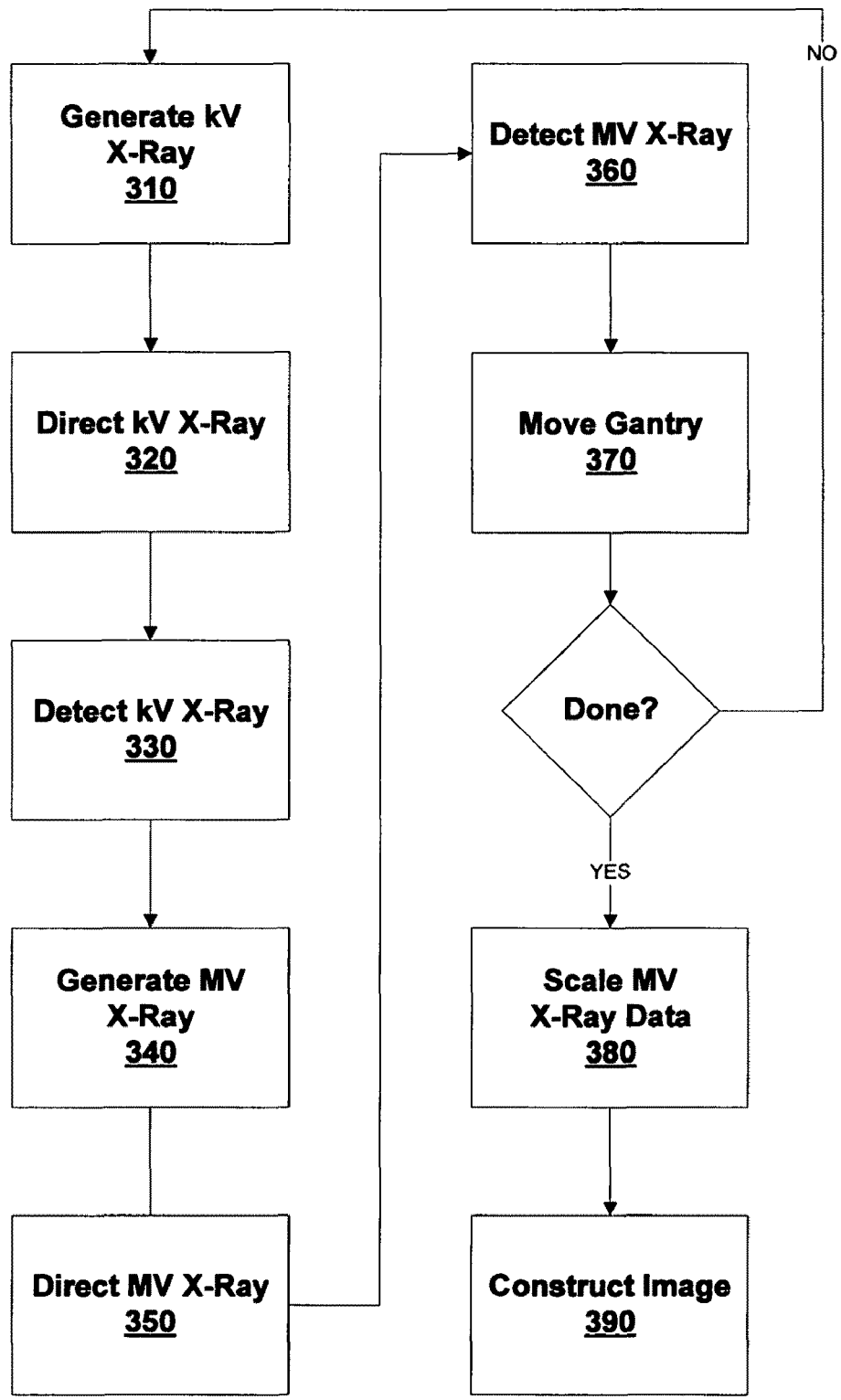
FIG. 3 is a flowchart illustrating methods of generating a three-dimensional representation of a target using the imaging system of FIG. 1, according to various embodiments of the invention.

FIG. 3 is a flowchart illustrating methods of generating a three-dimensional representation of Target 210 using Imaging System 100, according to various embodiments of the invention. In this method the kV source/detector combination and the MV source/detector combination are used to generate separate projection image data. Optionally, a first set of projection image data generated using one of these source/detector combinations is scaled such that it can be combined with a second set of projection image data generated using an other of these source/detector combinations. For example, the projection image data generated using the MV source/detector combination may be scaled such that it can be combined with projection image data generated using the kV source/detector combination. Following the scaling process, the scaled first set of projection image data and the second set of projection image data are used to construct a three-dimensional representation of Target 210.

In a Generate kV X-Ray Step 310, kV X-Ray Source 120 is used to generate x-rays in the kV energy range. In a Direct kV X-Ray Step 320, these kV x-rays are directed through Target Region 105 in order to image Target 210. Target 210 blocks passage of these kV x-rays as a function of the adsorption cross-section of Target 210. In a Detect kV X-Ray Step 330, those kV x-rays that pass through Target 210 are detected using kV X-Ray Detector 125. The detection of these x-rays includes generation, and optionally storage, of projection image data representative of a projection of Target 210 on kV X-Ray Detector 125.

In a Generate MV X-Ray Step 340, MV X-Ray Source 110 is used to generate x-rays in the MV energy range. In a Direct MV X-Ray Step 350, these MV x-rays are directed through Target Region 105. The MV x-rays can be used or imaging and/or treatment. In some embodiments, an aperture is used to reduce the volume within Target Region 105 that is exposed to the MV x-rays. While the volume within Target Region 105 that is exposed to kV x-rays and the volume within Target Region 105 that is exposed to MV x-rays are not necessarily the same, these volumes will typically overlap. Some of the MV x-rays are attenuated as they pass through an instance of Target 210 within Target Region 105. In a Detect MV X-Ray Step 360, those MV x-rays that pass through Target 210 are detected using MV X-Ray Detector 115. The detected x-rays are used to generate projection image data representative of a projection of Target 210 on MV X-Ray Detector 115. Detect kV X-Ray Step 330 and Detect MV X-Ray Step 360 optionally both include a phase in which projection image data is transferred from kV X-Ray Detector 125 and MV X-Ray Detector 115, respectively, to memory associated with Control Logic 140.

In an optional Move Gantry Step 370, Motor 135 is used to move Gantry 130. This movement rotates the kV source/detector combination and/or the MV source/detector combination relative to Target Region 105. In alternative embodiments, Motor 135 is used to move Target 210 while Gantry 130 remains stationary. Following Move Gantry Step 370, if further projection image data is required for the construction of a desired three-dimensional representation of Target 210, then the method returns to Generate kV X-Ray Step 310. If sufficient data has been generated for the construction of a desired three-dimensional representation of Target 210 then the method proceeds to a Scale MV X-Ray Data Step 380.

In some embodiments, Steps 310 through 370 are repeated numerous times in order to generate projection image data at a sufficient number of different projection angles to generate a desired three-dimensional representation. A projection angle is the angular position of an x-ray source around Target Region 105 relative to a fixed reference angle. For example, an angular position directly above Target Region 105 may be assigned 0 degrees while an angular position directly below Target Region 105 is assigned 180 degrees. The larger the number of different projection angles the greater the resolution of the three-dimensional representation, and the longer the imaging process takes. In some embodiments, Gantry 130 is rotated such that both MV and kV projection images are generated at overlapping projection angles. Typically, some or all of Steps 310-330 are performed in parallel in time (e.g., at times that are at least partially overlapping) with Steps 340-360. For example, any of Steps 310-330 may be performed parallel in time with Generate MV X-Ray Step 340. Thus, two different projection images, optionally using two different x-ray energies, can be generated at the same time. Thus, in some embodiments, kV X-Ray Source 120 and MV X-Ray Source 110 are used to generate x-rays simultaneously. In these embodiments, scatter correction is optionally used to reduce cross-talk between each source/detector combination. For example, in one embodiment, scatter correction is used to reduce the generation of noise at kV X-Ray Detector 125 resulting from x-rays generated using MV X-Ray Source 110 and scattered to kV X-Ray Detector 125 by Target 210.

Figure 4:
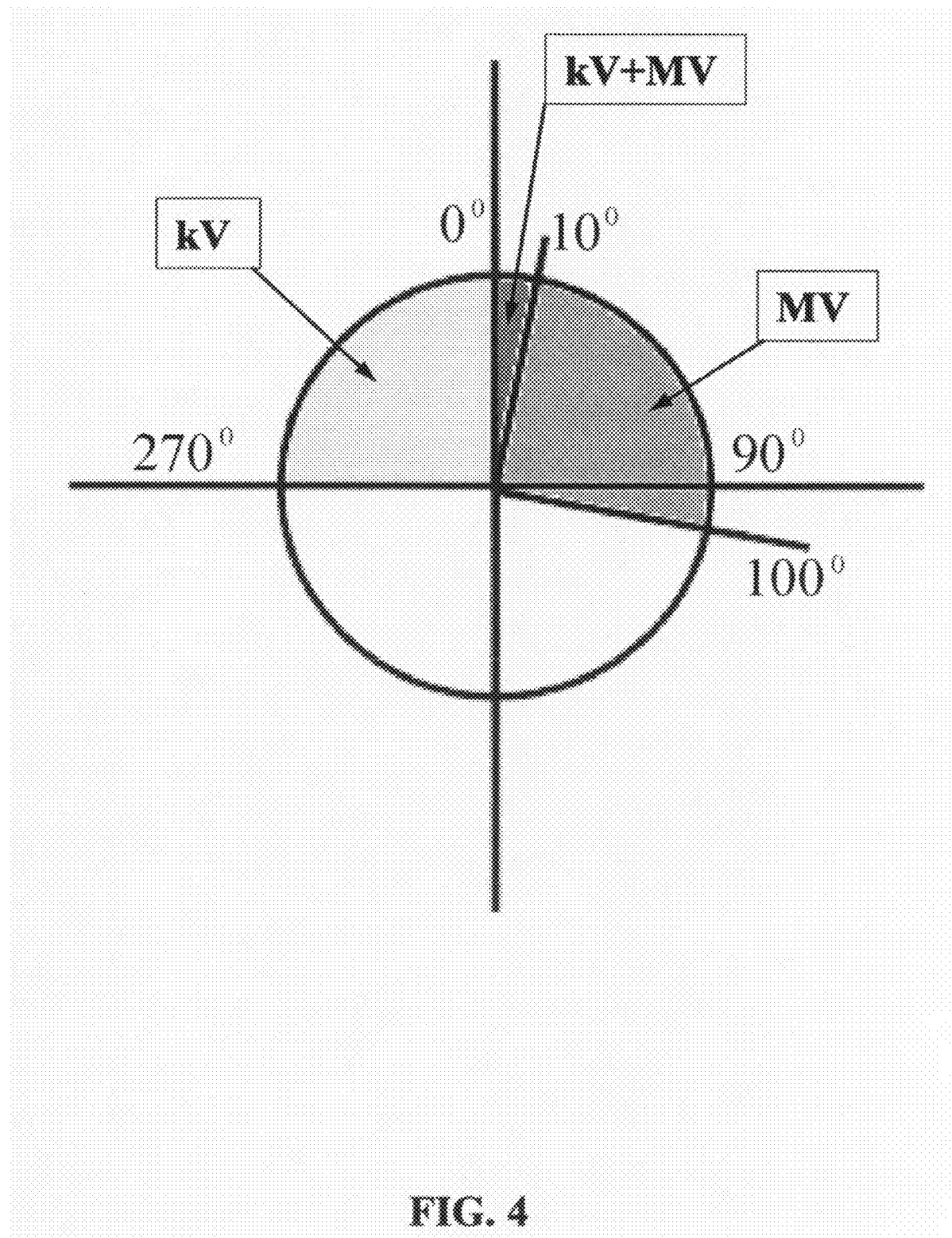
FIG. 4 is a graphical representation of projection angles used to generate projection images, according to various embodiments of the invention.

FIG. 4 is a graphical representation of projection angles used to generate projection images, in various embodiments of the invention. Relative to a projection angle arbitrarily labeled 0 degrees, kV X-Ray Source 120 is rotated to various projection angles between 270 degrees and 10 degrees by moving Gantry 130. At the same time, MV X-Ray Source 110, which is fixed at a position on Gantry 130 at a position approximately 90 degrees from kV X-Ray Source, is rotated to various projection angles between 0 degrees and 100 degrees. Using this rotation scheme, projection images are recorded between projection angles of 0 degrees and 10 degrees using both the kV source/detector combination and the MV source/detector combination. As is discussed further herein, the projection image data generated at these overlapping projection angles may be used to determine scaling factors for converting projection image data obtained using x-rays of one energy for combination with projection image data obtained using x-rays of the other energy.

Referring again to FIG. 3, in a Scale MV X-Ray Data Step 380 projection image data generated using MV X-Ray Detector 115 in Detect MV X-Ray Step 360 is scaled such that it can be combined with projection image data generated using kV X-Ray Detector 125 in Detect kV X-Ray Step 330. This scaling is performed using Conversion Logic 145. Typically, the scaling process involves multiplication of the projection image data by a scaling factor or application of a non-linear scaling function. In alternative embodiments, the kV projection image data is scaled for combination with the MV projection image data.

In a Construct Image Step 390, CT Construction Logic 150 is used to generate a three-dimensional representation of Target 210, or cross-section thereof, using both the scaled MV projection image data and the kV projection image data. The construction of the three-dimensional representation can be performed using any of the known algorithms for generating three-dimensional representations from two-dimensional projections known in the art of computerized tomography.

Cross-sections of the three-dimensional representation are optionally displayed to a user using Display 155.

Figure 5:
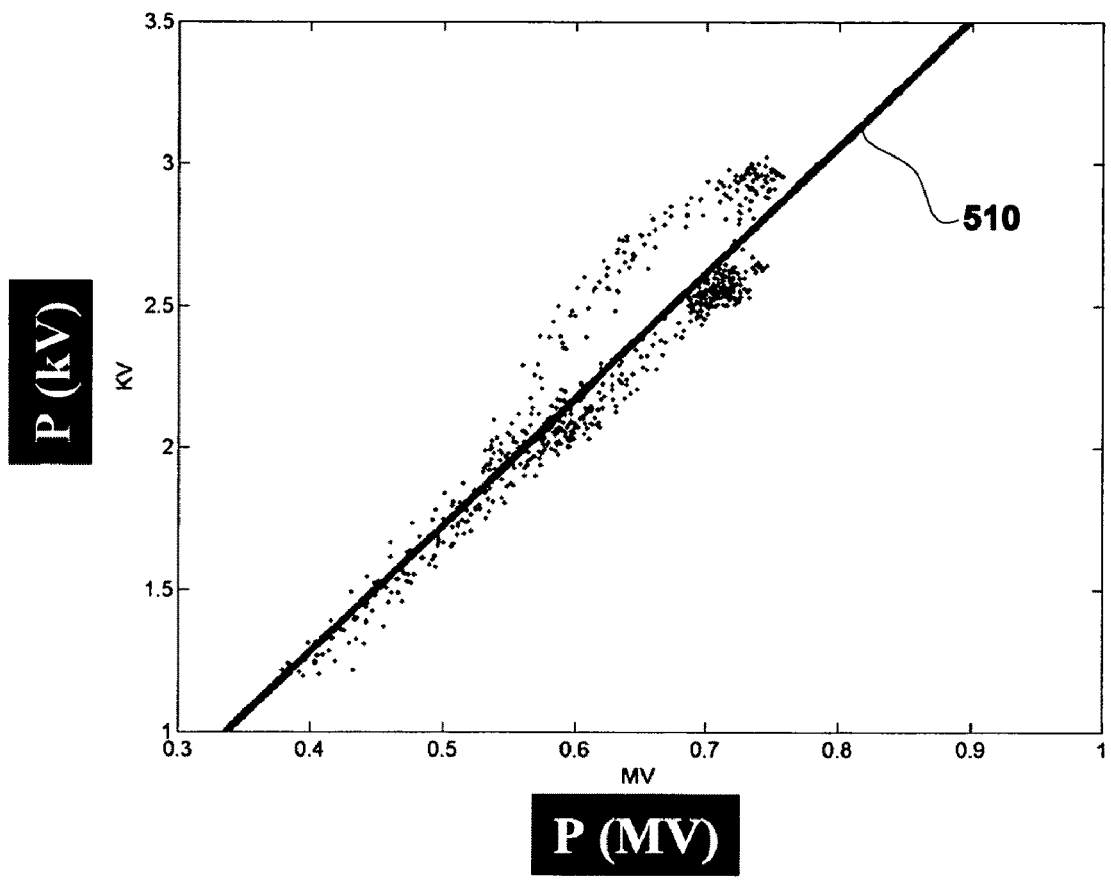
FIG. 5 is a scatter plot of kV and MV conversion parameters, according to one embodiment of the invention.

FIG. 5 is a scatter plot of kV and MV conversion parameters, according to one embodiment of the invention. These data are generated by comparing projection images obtained at the same projection angles using x-rays of two different energies, such as kV and MV energies. These same projection angles include, for example, the angles between 0 degrees and 10 degrees as shown in FIG. 4. Because, in some embodiments, the kV source/detector combination is oriented at a position approximately orthogonal to the MV source/detector combination, Gantry 130 (FIG. 1) is rotated 90 degrees in order for the MV source/detector combination to generate projection images at the same projection angles as the kV source/detector combination.

The scatter plot shown in FIG. 5 is generated by examining pixels in the MV projection images and noting the intensity of detected MV x-rays at those pixels. The corresponding pixels (e.g., the pixels representing the same positions) in the kV projection images are then examined and the intensity of the detected kV x-rays at those corresponding pixels are noted. In some instances, the noted values are normalized by dividing data obtained with an instance of Target 210 placed in Target Region 105 by data obtained without any target placed in Target Regions 105 (e.g., background data). The kV and MV intensity values are then plotted. A conversion parameter P for both kV and MV projection images is calculated using the formula $P = \log[(I_b - I_0)/(I_b - I)]$. Where $I_0$ was the pixel value from the open field and $I$ was the pixel value from the original projection image. $I_b$ was the background pixel value. This formula is based on an assumption that the radiation beam was attenuated exponentially through the imaging object. In FIG. 5 the plotted intensities have been fitted to a Line 510. Line 510 is optionally a linear function, in which case the slope and intercept can be used to convert MV projection image data to kV projection image data in Scale MV X-Ray Data Step 380 of FIG. 3.

Figure 6:
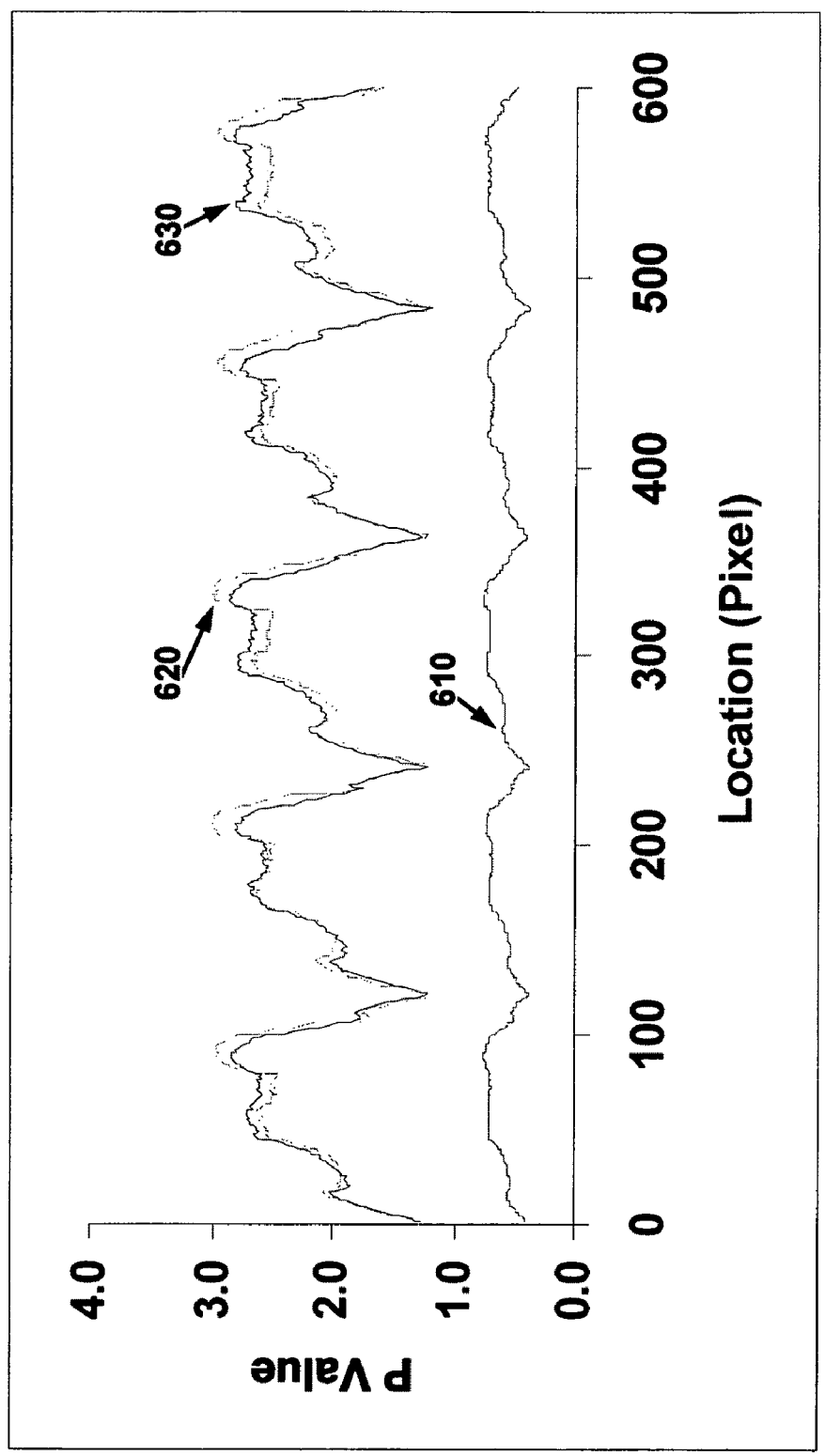
FIG. 6 illustrates the conversion of MV projection image data to kV projection image data, according to one embodiment of the invention.

FIG. 6 illustrates the conversion of MV projection image data to kV projection image data using the conversion parameter P calculated as discussed with respect to FIG. 5. The data shown represents a cross-section across a projection image. MV projection image data is represented by MV Line 610, kV projection image data is represented by kV Line 620, and converted MV projection image data is represented by Converted Data Line 630. Discrepancies between the kV profile and the converted MV profile in FIG. 6 are partially attributable to the use of a linear fit used to determine proportionality constant P. In alternative embodiments, a non-linear fit is used.

In various embodiments, different approaches are used to determine the conversion parameter P. For example, in some embodiments, projection images are acquired using a CT phantom having regions of different density. Because the regions within the CT phantom are well characterized, data taken using kV x-rays and MV x-rays can be compared typically at the same projection angle. Once the conversion parameter P is determined then a Target 210 of interest (e.g., a patient) is place in Target Region 110 and the previously determined conversion parameter P is used to convert the projection image data of the Target 210 of interest. In some embodiments, the conversion parameter P is determined using a less precisely characterized Target 210 of interest. In these embodiments, data obtained at overlapping projection angles are used to determine the conversion parameter P. In some embodiments, both a CT phantom and overlapping projection angles are used to determine conversion parameter P.

In some embodiments, the projection images generated using kV x-rays and MV x-rays are of different dimensions. For example, the volume covered by MV x-rays may be truncated such that it includes only a subset of the volume covered by kV x-rays. This arrangement may be desirable when the MV x-rays are used therapeutically and there is a wish to limit the exposure of healthy tissue to MV x-rays. Thus, in some embodiments of the invention, a larger target volume is covered by kV x-rays for the purpose of imaging Target 210 while a smaller target volume is covered by MV x-rays for the purpose of treatment. Further, those MV x-rays used for treatment are optionally also used to enhance the three-dimensional representation by combining the MV projection image data with the kV projection image data as described herein. Resolution of the three-dimensional representation is enhanced in the volume of Target 210 receiving therapeutic x-rays.

Figures 7A, 7B:
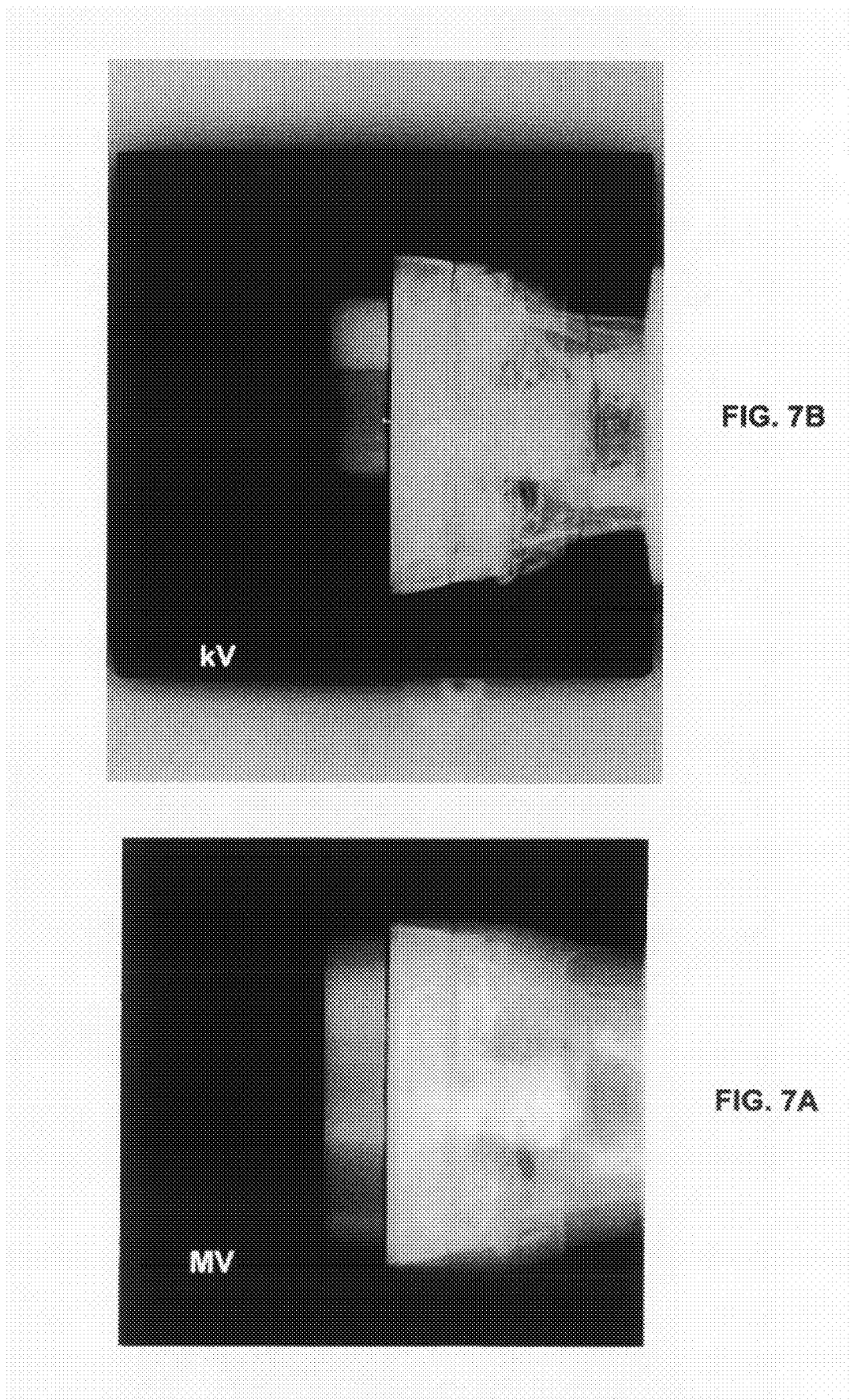
FIGS. 7A and 7B are CT images obtained using MV and kV imaging, respectively, according to one embodiment of the invention.

FIGS. 7A and 7B are CT images obtained using MV and kV imaging, respectively, according to one embodiment of the invention. A CT image is a cross-section of a three-dimensional object generated using computerized tomography. In this embodiment, projection images were acquired using a Varian Clinac 21EX accelerator (Varian Medical Systems) as MV X-Ray Source 110 to generate MV x-rays, and amorphous silicon electronic portal imager (a Si500 detector) as MV X-Ray Detector 115 to detect the generated MV x-rays. A Varian Medical System's On-Board Imager™ (OBI), including both kV X-Ray Source 130 and kV X-Ray Detector 125, was used to generate and detect kV x-rays. These systems were mounted orthogonally on Gantry 130 as shown in FIGS. 1 and 2. Three robotically controlled Exact™ (Varian Medical Systems) supportive arms were used to position MV X-Ray Detector 115, kV X-Ray Detector 125 and kV X-Ray Source 120 such that the beam lines of the MV source/detector combination and kV source/detector combination intersected orthogonally near the center of Target Region 105. The active imaging area for both kV and MV source/detector combinations was 397×298 mm. The matrix size for MV X-Ray Detector 115 was 1024×768 pixels with 2 bytes depth, and the matrix size for kV X-Ray Detector 125 could be either 2048×1536 pixels (high resolution) or 1024× 768 (low resolution) pixels with 2 bytes depth. A high-performance scatter rejection grid was mounted in the front of kV X-Ray Detector 125. The x-ray tube of kV X-Ray Source 120 had a target angle of 14 degrees and two focal spots: a nominal small spot of 0.4 mm and a nominal large spot of 0.8 mm, per IEC (International Electrotechnical Commission) 60336. The heat load capacity of this x-ray tube is 600 k heat units, while the heat loading of the x-ray tube housing is 2M heat units. The x-ray generator, within kV X-Ray Source 120, had a maximum output of 32 kW. Projection images acquired using the kV source/detector combination could be achieved with two different modes: digital radiography, both in high or low resolution, and digital fluoroscopic imaging with a frame rate of 7 or 15 frames per second. The kV source/detector combination also had a cone-beam CT acquisition mode which could acquire over 650 projections within less than 70 seconds. This mode is used for clinical applications.

In order to acquire the CT images shown in FIGS. 7A and 7B, a Target 210 was placed within Target Region 105. Target 210 included a head phantom and a contrast phantom taped together. The head phantom (RANDO® anthropomorphic phantom by Phantom Laboratories, Salem, N.Y.) and contrast phantom (Mini CT QC Phantom Model 76-430, Nuclear Associates, NY) are experimental tools configured to simulate a clinical instance of Target 210, such as a patient. The dimensions of the contrast phantom were six inches in diameter and one inch in thickness. The contrast phantom included insertions of different densities in six 1.125-inch circular holes. Projection images using the MV X-Ray Source 110 were acquired using gantry angles starting from 100 degrees to 270 degrees (IEC convention), with an interval of 2 degrees. The projection images using the kV source were acquired using gantry angles starting from 190 degrees to 0 degrees. A total of 96 projections were acquired at each x-ray energy. Because of the orthogonal relationship between of the MV source/detector combination and the kV source/detector combination, when MV X-Ray Source 110 was at 0 degrees, kV X-Ray Source 120 was at 270 degrees.

FIGS. 8A-8F include several cross-sections of three-dimensional representations (e.g., CT images) of one instance of Target 210 generated using the techniques described herein. FIG. 8A illustrates a CT image generated using 48 different MV projection images obtained at Gantry 130 angles between 100 degrees and 6 degrees. FIG. 8B illustrates a CT image generated using 48 different kV projection images obtained at Gantry 130 angles between 94 degrees and 0 degrees. FIG. 8C illustrates a CT image generated using both the 48 MV projection images used to generate FIG. 8A and the 48 kV projection images used to generate FIG. 8B. The kV and MV projection images were obtained and combined using, for example, the methods illustrated by FIG. 3.

The CT image of FIG. 8C includes more detail than either the CT images of FIG. 8A or 8B. This improved detail is due to the greater number of projections used and possibly the different sensitivities of the kV and MV x-rays. For example, the kV projection images show more contrast resolution for soft tissues while the MV images are less susceptible to some types of interferences.

FIGS. 8D and 8E include CT images. The CT image shown in FIG. 8D was generated using 96 different MV projection images acquired using Gantry 130 angles between 100 degrees and 270 degrees, and the CT image shown in FIG. 8E was generated using 96 different kV projections acquired using Gantry 130 angles between 190 degrees and 0 degrees. For comparison, FIG. 8F includes a diagnostic CT image, reconstructed by using almost 1000 projections acquired with a Philips AcQsim CT simulator.

Figures 9A, 9B, 9C:
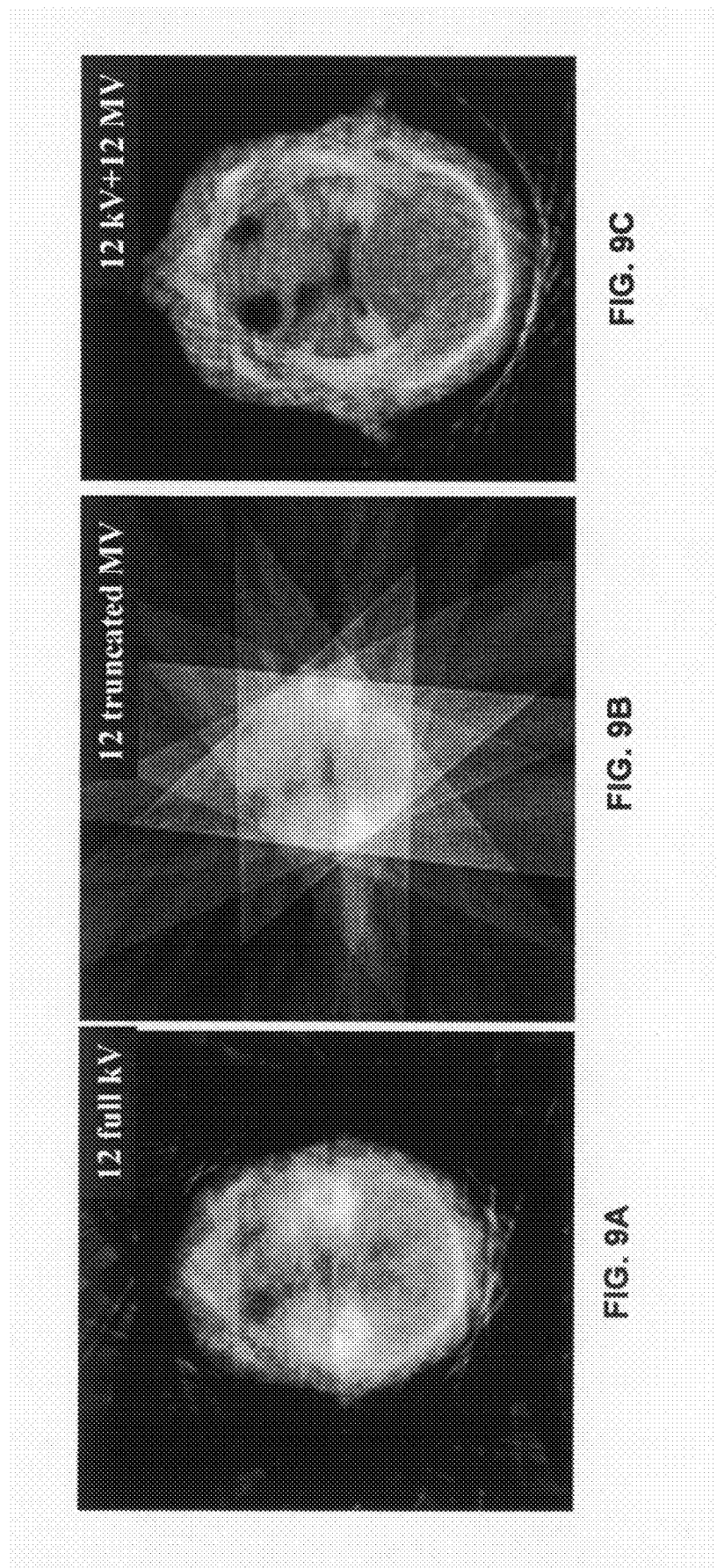
FIGS. 9A-9C include CT images generated using various imaging modes, according to one embodiment of the invention.

FIGS. 9A-9C illustrate the use of projection images that cover different volumes within Target 210. FIGS. 9A and 9B include CT images generated using only 12 full kV projection images, and only 12 truncated MV projection images, respectively. The MV projection images were generated using an x-ray beam truncated by an aperture to reduce the volume exposed to MV x-rays. In some embodiments, the MV x-rays are truncated to minimize the exposure of tissues outside a treatment volume to MV x-rays.

FIG. 9C includes a CT image generated using a combination of both the kV projection images used to generate the CT image of FIG. 9A and the MV projection images used to generate the CT image of FIG. 9B. As a result of the combination, the center region of the CT image of FIG. 9C is enhanced relative to that shown in FIG. 9A. Thus, MV treatment x-rays are combined with kV imaging x-rays to achieve greater CT image quality during treatment. This improvement may be used to refine the treatment volume and reduce the exposure of healthy tissue to harmful x-rays.

Several embodiments are specifically illustrated and/or described herein. However, it will be appreciated that modifications and variations are covered by the above teachings and within the scope of the appended claims without departing from the spirit and intended scope thereof. For example, while MV X-Ray Source 110 and kV X-Ray source 120 are used herein as an example, either may be replaced by alternative radiation sources. In some embodiments both sources are configured to generate the same types and/or energies of radiation. In some embodiments, the methods discussed herein are used to generate four-dimensional CT data that includes a time dependent three-dimensional representation of Target 210. In some alternative embodiments, projection images generated using a kV source/detector combination are used to generate a first three-dimensional representation, and projection images generated using a MV source/detector combination are used to generate a second three-dimensional representation. The first and second three-dimensional representations are then combined using CT Construction Logic 150 to form one or more CT images. In these embodiments, Scale MV X-Ray Data Step 380 and Conversion Logic 145 are optional. In some embodiments, more than two source/detector combinations are used to generate projection images parallel in time. Control Logic 140, Conversion Logic 145 and/or CT Construction Logic 150 are each optionally embodied in hardware, firmware, or software stored in memory.

In some embodiments, the projection images generated using one or more of the source/detector combinations are each one pixel line, e.g., one-dimensional. These projection images are each representative of the attenuation of x-rays along a line through Target Region 105. In these embodiments, a plurality of one-dimensional projection images may be used to generate a two-dimensional representation of Target 210, using the systems and method of the invention. The adaptation of the systems and method of the invention to the generation of two-dimensional representations from one-dimensional projection images would be apparent to a person of ordinary skill in the art.

In some embodiments, MV projections are generated using x-rays configured for x-ray treatment of a patient. In these embodiments, a computerized tomography image constructed using kV projection image data and MV projection image data may be used for identifying and/or viewing the treatment volume. In these embodiments, MV x-rays are used for both treatment and imaging.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

Exact™ and On-Board Imager™ are registered trademarks of Varian Medical Systems, Inc.

I claim:
1. A system comprising:
   a first x-ray source configured to generate x-rays having energies in a first range;
   a first imaging x-ray detector configured to detect the x-rays in the first range and to generate resulting first projection image data of a target;
   a second x-ray source configured to generate x-rays having energies in a second range, wherein one of the first range and the second range is a MV range;
   a second imaging x-ray detector configured to detect the x-rays in the second range and to generate resulting second projection image data of the target, the target disposed at an intersection of a first axis between the first x-ray source and the first imaging x-ray detector and a second axis between the second x-ray source and the second imaging x-ray detector;

a conversion logic configured to convert the second projection image data to be compatible with the first projection image data and a logic configured to generate a computerized tomography image using the first projection and the second projection image data.

2. The system of claim 1, wherein the first energy range is the MV range and the second energy range is a kV range.

3. The system of claim 1, wherein the first energy range is a kV range and the second energy range is the MV range.

4. The system of claim 1, wherein the first axis is approximately orthogonal to the second axis.

5. The system of claim 1, wherein the first imaging x-ray detector and the second imaging x-ray detector are configured to operate in parallel in time.

6. The system of claim 1, further including a motor configured to move the first x-ray source to a first set of positions and the second x-ray source to a second set of positions.

7. The system of claim 6, wherein the first set of positions and the second set of positions include some positions in common.

8. A method comprising:
generating first x-rays in a first energy range;
directing the first x-rays through a target;
detecting the first x-rays to produce first projection image data representative of the target;
generating second x-rays in a second energy range, wherein the first energy range and the second energy range include at least a MV energy range and a kV energy range;
directing the second x-rays through the target;
detecting the second x-rays to produce second projection image data representative of the target, wherein at least one image of each of the first projection image data and the second projection image data is taken at same projection angle relative to the target; and
constructing a computerized tomography image using the second projection image data and the first projection image data.

9. The method of claim 8, wherein at least one of the acts of generating first x-rays and detecting the first x-rays is performed in parallel in time with at least one of the acts of generating second x-rays and detecting the second x-rays.

10. The method of claim 8, wherein the act of generating first x-rays and the act of generating second x-rays are performed parallel in time, and scatter correction is used to reduce noise resulting from scattered x-rays.

11. The method of claim 8, wherein the act of generating first x-rays is performed at a first series of projection angles relative to the target, and the act of generating second x-rays is performed at a second series of projection angles relative to the target.

12. The method of claim 11, wherein the first series of projection angles and the second series of projection angles include at least one projection angle in common.

13. The method of claim 8, wherein the first x-rays are therapeutic, and the first projection image data are used to improve resolution in a computerized tomography image through combination with the second projection image data.

14. The method of claim 8, wherein a volume in the target exposed to the first x-rays is smaller than a volume in the target exposed to the second x-rays.

15. A system comprising:
means for generating and detecting first x-rays to generate first projection image data representative of a target;
means for generating and detecting second x-rays to generate second projection image data representative of the target, the means for generating and detecting the second x-rays being configured to either generate the second x-rays of different energies than the first x-rays, or generate and detect the second x-rays parallel in time with the generation and the detection of the first x-rays;
means for converting the first projection image data and the second projection image data to be compatible; and
means for generating a CT image using the first projection image data and the second projection image data.

16. The system of claim 15, further including means for identifying a treatment volume using a treatment beam.

17. A system comprising:
a first x-ray source configured to generate x-rays having energies in a MV range;
a first imaging x-ray detector configured to detect the generated x-rays having energies in the MV range modified by an aperture to generate resulting first projection image data of a target in partial;
a second x-ray source configured to generate x-rays having energies in a kV range;
a second imaging x-ray detector configured to detect the x-rays in the kV range and to generate resulting second projection image data of the target, wherein the first projection image data and the second projection image data are of different dimensions, the target disposed at an intersection of a first axis between the first x-ray source and the first imaging x-ray detector and a second axis between second x-ray source and the second imaging x-ray detector; and
a logic configured to generate a computerized tomography image using the first projection image data and the second projection image data.

18. A method comprising:
generating first x-rays in a MV energy range;
modifying the first x-rays by an aperture,
directing the modified first x-rays through a target in partial;
detecting the first x-rays to produce first projection image data of partial representative of the target;
generating second x-rays in a kV energy range;
directing the second x-rays through the target;
detecting the second x-rays to produce second projection image data representative of the target;
constructing a computerized tomography image using the first projection image data and the second projection image data.

* * * * *